(12) United States Patent
Schaible et al.

(10) Patent No.: US 8,306,656 B1
(45) Date of Patent: Nov. 6, 2012

(54) METHOD AND SYSTEM FOR PERFORMING MEDICAL PROCEDURE

(75) Inventors: Uwe Schaible, Ancaster (CA); Jeff Veltri, Burlington (CA); Amin Ahmadi, Mississauga (CA)

(73) Assignee: Titan Medical Inc., Toronto, Ontario (CA)

( * ) Notice: Subject to any disclaimer, the term of this patent is extended or adjusted under 35 U.S.C. 154(b) by 417 days.

(21) Appl. No.: 12/655,675

(22) Filed: Jan. 5, 2010

Related U.S. Application Data (60) Provisional application No. 61/204,838, filed on Jan. 12, 2009.

(51) Int. Cl.
*G06F 19/00* (2006.01)

(52) U.S. Cl. ...................................................... 700/245

(58) Field of Classification Search .................. 700/245, 700/250, 257, 264; 606/1
See application file for complete search history.

(56) References Cited

U.S. PATENT DOCUMENTS

| | | | |
|---|---|---|---|
| 7,453,227 B2 * | 11/2008 | Prisco et al. | 318/568.11 |
| 2004/0111183 A1 | 6/2004 | Sutherland et al. | |
| 2004/0116906 A1 | 6/2004 | Lipow | |
| 2010/0063630 A1 | 3/2010 | Sutherland et al. | |

\* cited by examiner

*Primary Examiner* — Faye M. Fleming
(74) *Attorney, Agent, or Firm* — Perry + Currier Inc.

(57) ABSTRACT

The present application describes a method and system for performing medical procedures. The system includes a robotic arm assembly, an end effector assembly and a set of transducers. The system further includes a cable element that is used to control the movement of the robotic arm assembly and the end effector assembly. The cable element is also connected to the set of transducers, which measure the force imparted on the robotic arm assembly and the end effector assembly during the medical procedures.

20 Claims, 6 Drawing Sheets

METHOD AND SYSTEM FOR PERFORMING MEDICAL PROCEDURE

CROSS REFERENCE TO RELATED APPLICATION

This application claims priority of U.S. Provisional Application No. 61/204,838 filed Jan. 12, 2009 which is incorporated by reference herein.

FIELD OF INVENTION

The present application relates to the field of robotic instruments, and more particularly to robotic instruments for performing medical procedures.

BACKGROUND

In the field of medical surgery, conventional processes involve making long incisions on the patient's body. For example, in a cardiac surgery of the coronary artery, the patient's chest is opened and the surgery is performed on the heart. In the present days, these are being replaced by Minimally Invasive Surgery (MIS). In MIS, instead of long incisions, small incisions are made for enabling an operating equipment to enter the patient's body and perform the surgery.

MIS is performed by using a robotic instrument assembly that typically includes straight, elongated shafts (hereinafter referred to as robotic arms), operational and/or monitoring equipment (hereinafter referred to as end effectors) and a console. The operational equipment is used to perform the medical procedures, such as scissors for cutting a tissue. Monitoring equipment, such as a camera or microphone, assist the operator in performing MIS. The console is used to control the motion of the robotic arm and the operational equipment. The inputs for controlling the components of the robotic instrument assembly are provided through a hand controller present in the console.

Further, the robotic instrument assembly includes a motor drive unit and a haptic feedback system. The motor drive unit is configured for inducing tensile forces in the drive element and articulating the movement of the robotic arms and the end effectors, thereby enabling the movement of the robotic arm in multiple degrees of freedom. The haptic force feedback is used by the operator during the surgical procedure to estimate the magnitude of the pressure that needs to be applied at the surgical site. The haptic feedback unit measures forces acting on the robotic arm and end effector assembly and uses these measured forces to produce the haptic force feedback characterized by counter forces and vibrations at the hand controller.

The value of the measured forces acting on the robotic arm and end effector assembly can be affected by several environmental and internal factors. These factors include tool-tissue engagement, tool tip vibrations, and vibrations arising from the mechanical assembly of the motor drive. Due to these factors, the measured forces include unwanted noise. In the present state of the art, the system does not include any arrangement to remove the noise generated due to environmental factors, thus leading to generation of an erroneous force feedback. Therefore, an operator is not able to correctly estimate the precise pressure required for performing the procedures. When the operator uses the incorrect estimate, the procedures may not be performed accurately, and may lead to injuries such as tissue damage.

SUMMARY

In light of the foregoing discussion, there is a need for a method and integrated robotic arm system with an efficient drive system for driving the robotic arm and the end effectors, and an accurate haptic feedback unit so as to provide a virtual surgery environment that is as real as possible. This, in turn, will reduce the requirement of human judgment and hence, the probability of errors.

BRIEF DESCRIPTION OF THE DRAWINGS

The preferred embodiments of the invention will hereinafter be described in conjunction with the appended drawing provided to illustrate and not to limit the invention, wherein like designations denote like elements, and in which.

DETAILED DESCRIPTION OF THE INVENTION

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention.

Figure 1:
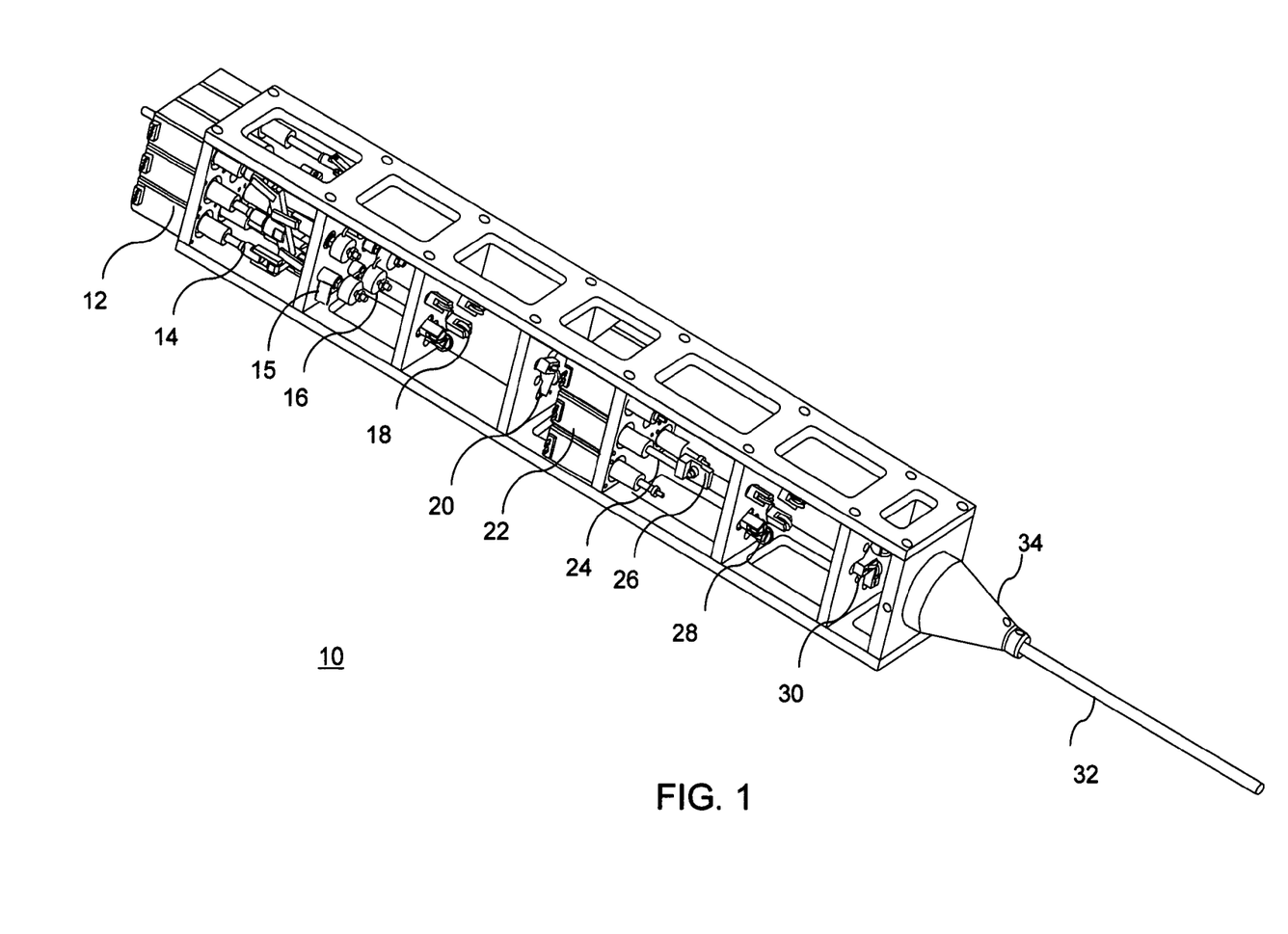
FIG. 1 illustrates a perspective view of a robotic motor drive and haptic feedback system, in accordance with an embodiment of the present invention.

FIG. 1 illustrates a Robotic Motor Drive and Haptic Feedback System 10 for use in a medical procedure, such as a Minimal Invasive Surgery (MIS). The system uses precision actuators, eg, 12 and 22, to move and induce tensile forces in a mechanical drive unit comprising cables and pulleys, eg, 18 and 20, and which, in turn, transmit motion for articulating the robotic arm (not shown) and end effector assembly (not shown) connected to the robotic arm. An end effector assembly is an assembly of medical tools/equipment as described above. In an embodiment, the precision actuators can be linear actuators. In the same or another embodiment, the precision actuators can be motors. The term motor and actuator have been hereinafter used interchangeably. Additionally, the system 10 makes use of force transducers eg, 16, to measure forces acting on the joints of the robotic arm and the end effector assembly and generate signals corresponding to the measured forces. Furthermore, the signals generated by the force transducers are transmitted to a robotic hand controller (not shown) where haptic force feedback, in the form of vibration and counterforces, is generated by motors (not shown) present in the exoskeleton of the robotic hand controller. The said force feedback thus assists the user to apply optimum pressure on the tissue and sutures. In an embodiment, the force transducers are mounted on the same cable elements (shown in FIG. 2) that are used in the drive unit of the system 10. The force transducers estimate the said forces by measuring tension loads acting on the cable elements.

Figure 5:
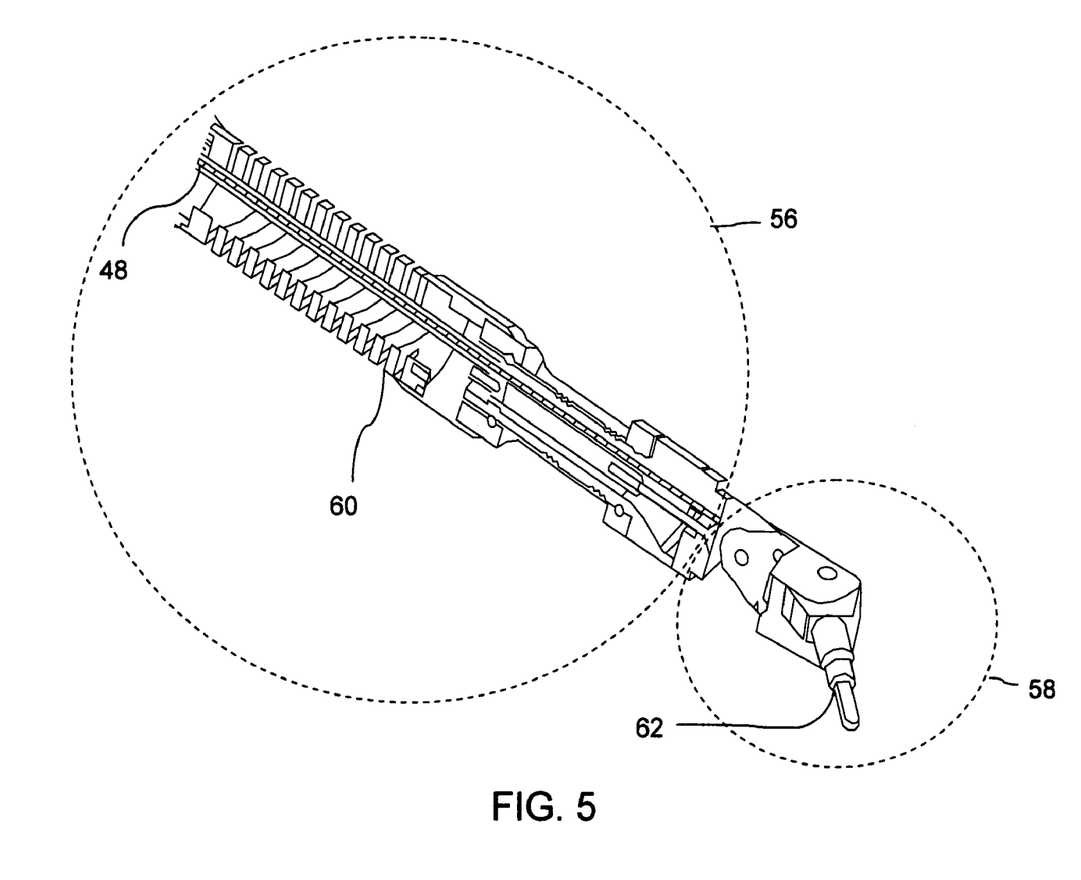
FIG. 5 illustrates one of the possible arrangements of the cable inside the robotic arm of the robotic motor drive and haptic feedback system, in accordance with an embodiment of the present invention.

In order to access different points within the site of surgery, the operator has to articulate the robotic arm, and has to position it accurately over the localization point, i.e., the site which needs to be operated on. Thereafter, the end effector assembly has to be positioned and oriented in space in a manner such that it gets proximal to the localization point. The robotic arms in the current state of the art are known to comprise joints. These joints can be moved to achieve the desired articulation of the robotic arm in the available X, Y and Z planes of a co-ordinate system. The joints and the elongated shaft like robotic arm are as depicted in FIG. 5. Additionally, the end effectors are capable of generating a pitch, yaw, roll and pincer action. Combining the motion of the robotic arm and the end effectors, motion in numerous degrees of freedom can be achieved.

Figure 2:
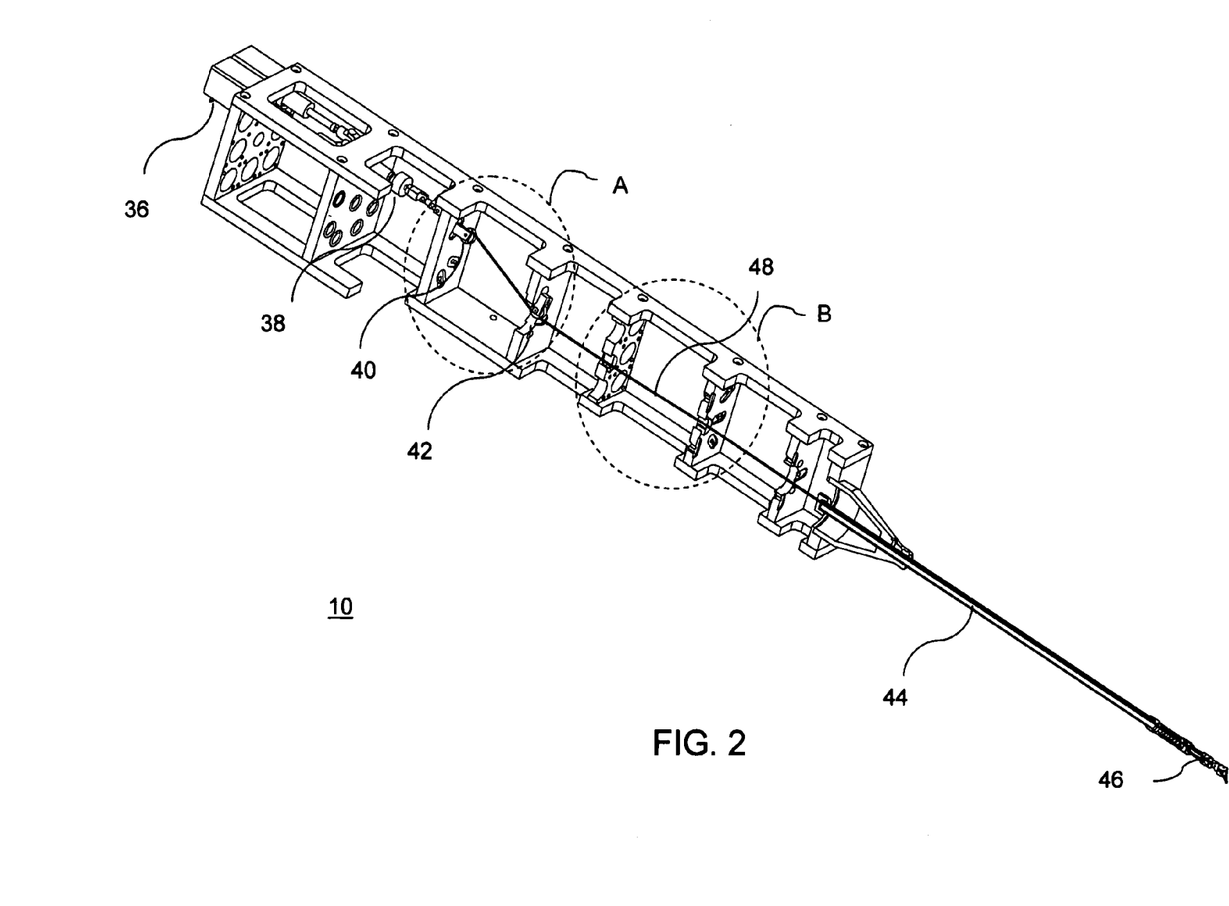
FIG. 2 illustrates one of the possible arrangements of the cable inside the robotic motor drive and haptic feedback system, in accordance with an embodiment of the present invention.

The positioning for reaching the exact area at the site of surgery is done by actuating the first and second set of motors present in the joint drive assembly 24 and tool drive assembly 14, respectively. The motors in turn achieve the proper positioning by transmitting the motion through the cable elements (not shown) in the system, which are as described with the help of subsequent figures. First, the robotic arm joints, described below with reference to FIGS. 2 and 5, are driven with the help of one or more of the motors from the joint drive actuator assembly 24 which vary the tension in the cable element to drive the joints. The movement of the joints, in turn, takes the robotic arm proximal to the site of surgery. Hence, it can be said that the cable element controls the movement of the robotic arm. The driving of the robotic arm joints with the help of one or more motors is achieved by performing a joint control procedure. At first, the tension in the cable elements, passing through the joints, is decreased by moving the one or more motors from a high locking tension level (X) to another appropriate unlocking low tension level (Y) according to the intended motion. This procedure is called "unlocking" since this enables the joint cable elements to lower their inertia to be pulled easily in a certain direction. Thereafter, the one or motors are further actuated and the robotic arm joint is moved to reach its desired position. After the robotic arm has been positioned, the one or more motors are actuated again to increase the tension in the cables from a Level Y to Level X in order to lock the assembly in that position. The locking is desirable to provide a sturdy and stable platform to position the end effector to perform the surgical procedure. The tension level or the magnitude of tensile forces which needs to be induced in the cable elements ranges from a level X to a level Y and is a pre-determined value. In an embodiment, software procedural algorithms can be embedded in the system to automate numerous operations which the operator performs manually. Software procedural algorithms can be used to replicate a given set of instructions similar to the joint control procedure described above to predict joint movements to ease the manoeuvring of the joints. The Software procedural algorithms enable the different functionalities to be programmed and subsequently used to follow both planned and learned paths for auto-inserting and auto-retracting the end effector. Essentially, the planned path is the manual course of instruction as given by a user to move the end effector, whereas the learned path course provides the user with the ability to record the frequently used manoeuvres or actions and replay them while performing a surgical operation whenever a need arises. The learned path course not only eliminates the need of manual action and the possibility of any error associated thereof but also performs the operation quickly and efficiently. In other words, the learned path enables auto-inserting and auto-retracting controls which remember the positions of all end effector and joint control movements performed manually by the user, and then enable the performance of the registered steps automatically. Software control can also remove the unnecessary steps or wait periods to further accelerate the auto-inserting and auto-retracting process. Here, auto-retract and auto-insert controls signify automatic retraction of one existing end effector out of the patient body and insertion of the next end effector into the body along the same path. It is also possible to embed software control algorithms to control a coordinated movement of multiple joints, and to monitor and control joint force. These algorithms can achieve this directly through force transducers present on the cable element for the joint, or indirectly through control of the motor winding current.

In a manner similar to the joint control procedure, an end effector control procedure is performed to move the end effector, with the help of one or more motors from the tool drive assembly 14, to the operating point within the site of surgery. This is performed by pre-tensioning all end effector control cable elements by raising the force to a level (Z) and then moving the one or more motors to actuate the roll, pitch, yaw, open/close movements (pincer) of the end effector. After the end effector has been moved to the correct position, the tension in the cable is increased to a level (A) to lock the end effector in that position. Here, the levels Z and A are similar to levels X and Y, respectively, of the joint control procedure, but can have a varying magnitude. Software procedural algorithms can be embedded in the system to synchronize the pincer movements of various end effectors to create coupled pincer movement.

Further, after appropriate positioning of the end effector, and as the surgical intervention commences, a haptic force feedback signal is generated to provide the user a real feel of the forces acting at the site of surgery. This is accomplished by measuring the differential force between each end effector-cable element pair using the force transducers, e.g., 16. Software procedural algorithms can be provided to map the forces measured by the force transducers to the real-time 3-dimensional model of the articulated robotic arm configuration. The compared output haptic force is thus resolved through a set of co-ordinate transformations and is filtered to provide a decoupled haptic feedback for the various degrees of freedom of the robotic arm assembly. The need for filtering the measured and mapped force signal is described in the following discussion.

As can be seen from the above discussion, the cable elements used in the present invention have dual usage, i.e., to drive the robotic arm or the end effector and to achieve force transduction for the degree of freedom in question. As the cable element drives the robotic arm, inherent friction arises from the mechanical sources present in the drive system 10. Some mechanical sources present are the guide pulleys and the cable elements themselves. Further, friction arises from the end effector tool—tissue interface. In the present invention, as the force transducers connected to the cable element sense and measure forces acting at the end effector, the inherent friction forces that are imparted by the environment and the mechanical sources are filtered out to get an error free signal. For this purpose, signal filter 15 can be used in the system 10 to separate noise from the measured force signal. In an embodiment, the signal filter 15 is a band-pass filter. In another embodiment, the signal filter 15 is a high pass filter readily known to a person of ordinary skill in the art. The signal measured by the force transducers is given to a control system including the high-pass filter. The control system accepts an overall signal drift from the force transducer and provides only 'spikes' of signal change to the robotic hand controller by performing high-pass filtering. The high pass filter lets the high frequency present in the signal pass to the robotic hand controller and attenuates the low frequencies. Thereafter, the signal is fed to a haptics capable hand controller where it is interpreted and an accurate force feedback is given to the user. The compensations made for the frictional forces can also be learned or predicted for a certain configuration of the articulating arm in a manner similar to the joint control procedure. In other embodiments, the placement of the signal filter 15 can be different from that shown in FIG. 1. In yet another embodiment, the signal filter 15 can be external to the system 10.

It should be appreciated that, in an embodiment of the present invention, a single cable element is responsible for driving a robotic arm joint and the end effector associated with it. Further, the transducers are also mounted in connection to the same cable element and sense the force acting on it that acts as an input for generation of the haptic force feedback.

In an embodiment, a cable element can have one motor for tensioning and one motor to drive a pivoting arm that moves the cable element. The two independent motors (linear actuators) can then be electronically coupled through a precision drive system and software to synchronize their motions and dynamically adjust the cable element tensions. The dynamic tensioning of the cables during synchronized movement may allow for improved haptics isolation from the static friction forces. In another embodiment, each motor of the tool drive assembly 14 or the joint drive assembly 24 can independently move and tension one cable element. In yet another embodiment, the set of motors can be completely replaced with passive springs which can tension the cable elements.

In one embodiment the present invention, haptic feedback resolution can be enhanced by providing minimum length conduit paths, minimal contact/friction points, PTFE or other low friction coatings on cables and conduits, and internal roller bearings at pulley guides. These features help to reduce the inherent friction caused by the environment and the mechanical assembly and thus make the force feedback more accurate.

The method for transmitting motion from the motor drive to the robotic arm and the end effector, and sensing force feedback through the same cable element is accomplished by using system 10 as shown in FIG. 1 which includes a plurality of triad units. The triad unit is formed by a linear actuator, a force transducer and a cable element. The Robotic Motor Drive and Haptic Feedback System 10 of FIG. 1 includes two sets of linear actuators, the first set (represented by 24) for providing transmission to the robotic arm joints and the second set (represented by 14) for articulating the end effector. A single degree of freedom of movement of the robotic arm and the corresponding end effector can be achieved by actuating either or both of the first set of motors or/and the second set of motors. Further, each degree of freedom has a separate triad associated with it.

As shown in FIG. 1, a triad unit used for articulating the end effector in one of its degrees of freedom and sensing the forces associated with that degree of freedom is composed of an end effector actuator selected from a set of tool drive linear actuators, represented by 14, a force transducer selected from a group of force transducers including 16, and a cable element selected from a group of cable elements (not shown). The selected end effector actuator is connected to the cable element to drive the end effector, as described earlier. The force transducer 16 is also attached to the cable element. Further, the cable element is made to pass through the pulleys, such as 18 and 20, into the middle of a guide tube 32, and finally connects to the robotic arm and the end effector which it controls. One of the possible paths of a cable element through the system 10 has been depicted in FIG. 2. The force transducer 16, as described earlier, measures any environmental forces imparted on the end effector pertaining to the degree of freedom being controlled, converts the measured forces to a signal, and relays the signal to a robotic console where the user sits. An appropriate haptics capable hand unit converts the signal received into vibrations and counter forces to provide the force feedback signal to the operator. Therefore, to drive each individual degree of freedom of the multiple degrees of freedom of a robotic arm, a separate triad unit is preferably present in the system. Hence, one or more such units are housed within the Robotic Motor Drive and Haptic Feedback System 10 depending on the total degree of freedom articulating capability of the robotic arm.

For the articulation of the robotic arm around its pivot axis in the translational planes (X, Y, Z of a three dimensional coordinate system), a robotic arm actuator from the set of joint driving actuators, represented by 24, is used. In one embodiment, the robotic arm actuator will be connected to one of the force transducers e.g., 16 and a cable element passing through the cable clamp 26 to form a triad unit, and thus articulate, sense and measure force for haptic feedback as mentioned above in the case of the end effector assembly. The cable element is made to pass through its corresponding pulleys, such as 28 and 30, into the middle of the guide tube 32, and then is connected to the robotic arm joint which it intends to control. In another embodiment of the present invention, the cone plate nose assembly 34 may contain force transducers within the cone plate nose 34 to sense the forces acting in the translational planes X, Y, and Z of the robotic arm. The output signal from the force transducers present in the cone plate nose 34 is passed to the control system for filtering any noise present. This process of filtering has been described above. It will be readily apparent to a person of ordinary skill in the art that force sensing, the placement of the transducers and joint articulation can be achieved by a method other than those described above.

FIG. 2 is a perspective view of the Robotic Motor Drive and Haptic Feedback System 10 illustrating one of the possible paths of the cable element through the various components of the system 10. The cable element 48 is a part of the triad unit which is described above. The cable element 48 is shown to be connected to an end effector actuator 36 selected from a set of tool drive linear actuators 14, and a force transducer 38 selected from a group of force transducers. Further, the cable element 48 is shown to be passing through the pulleys 40 and 42 which are selected from a group of pulleys, into the middle of the guide tube 44, and to a corresponding robotic arm and end effector assembly, collectively represented by 46, which are controlled by the triad unit of which the cable element 48 is a part. The principles corresponding to the articulation of the robotic arms and the end effectors and the sensing of forces acting at the end effector have been described in regard to FIG. 1.

Figure 3:
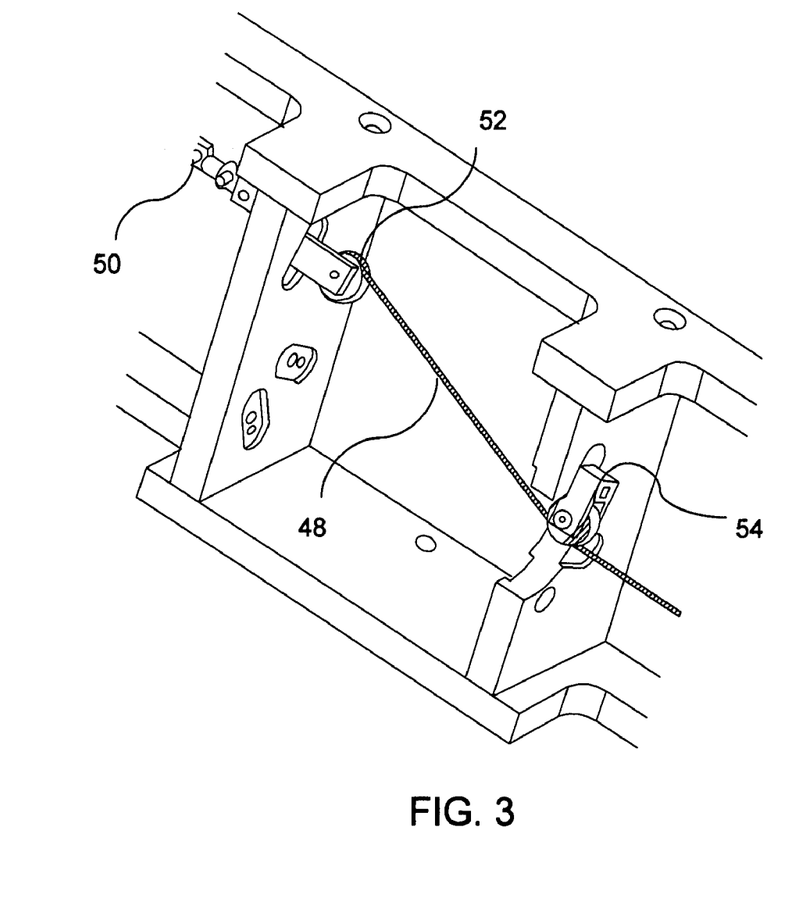
FIG. 3 illustrates one of the possible arrangements of a cable element inside a section of the robotic motor drive and haptic feedback system, in accordance with an embodiment of the present invention.
Figure 4:
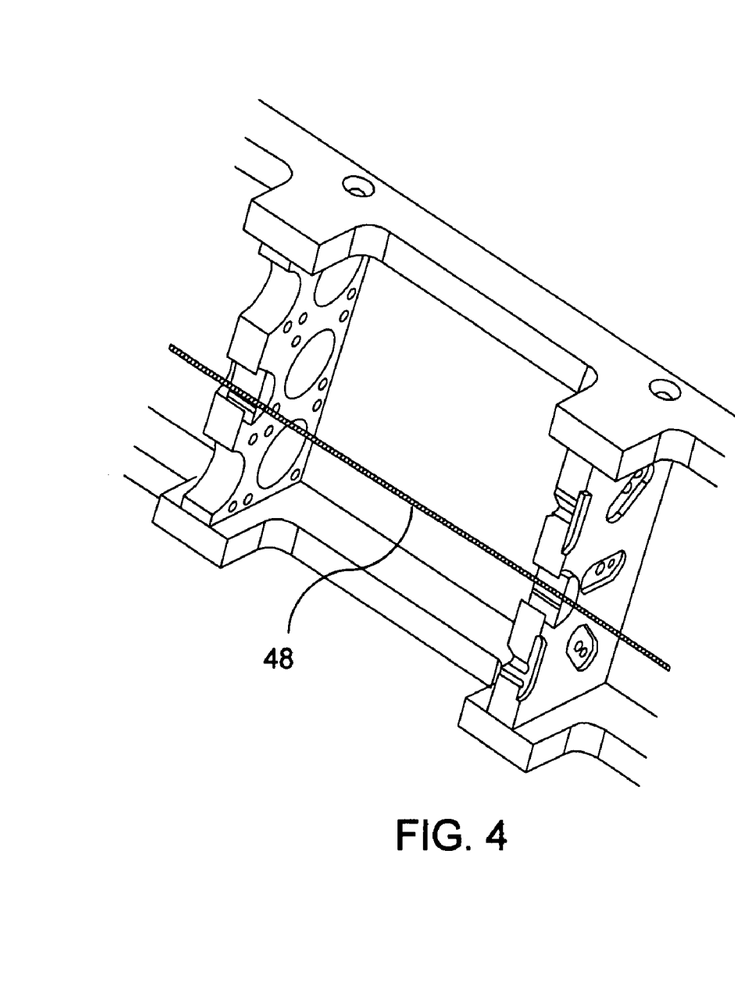
FIG. 4 illustrates one of the possible arrangements of a cable element inside a section of the robotic motor drive and haptic feedback system, in accordance with an embodiment of the present invention.

FIG. 3 illustrates a magnified view of area A depicted in FIG. 2. FIG. 3 depicts one of the possible arrangements of the cable element 48 inside the Robotic Motor Drive and Haptic Feedback System 10. The cable element 48 is shown to be connected to a force transducer 50, and thereafter passing through two pulley arrangements 52 and 54. Similarly, FIG. 4 illustrates magnified view of area B depicted in FIG. 2.

FIG. 5 illustrates one of the possible arrangements of the cable element 48 inside the Robotic arm 56 of the Robotic Motor Drive and Haptic Feedback System 10. The cable element 48 is shown to be passing through the robotic arm 56 and connects to an end effector assembly 58. The robotic arm 56 is shown to have joints, represented by 60 while the end effector assembly is shown to have an end effector 62.

In an embodiment, the motors used for the movement of the end effector and robotic arm joints are the series 28000, Size 11 Double Stack Linear Actuators from Haydon Switch & Instruments. The motors for the end effector movement use the model 28M41-05-912, 5V DC, 0.42A per phase, 0.001" step, 1.25" stroke Linear Actuators. This motor provides excellent speed at moderate force levels. The motors for robotic arm joint movement use the 28M47-05-910, 5V DC, 0.42A per phase, 0.000125" per step, 1" stroke Linear Actuators. The smaller step size version gives much higher force for tensioning the joint cables at the expense of slower joint movement. Hence, joint control speed can be made slower than end effector control speed.

In an embodiment, the force transducers used in the system for force feedback signal generation are the Omega LCMFL-50N, Sub-miniature tension compression load cell. In this embodiment, Omega LC201-50, Sub-miniature tension compression load cell is used for measuring force/tension levels on the joint cables and AL312BL, Sensotec Model 34 load cell is used in the form of three sensors arranged in a triangle to measure the force at the cone as described above.

It will be readily apparent to a person of ordinary skill in the art that the shape and form of the motor drive and haptic feedback system can be obtained from several options. Further, details of cable placement, transducer placement, housing and arrangement of the motors and cables, and overall weight and dimensions can be changed on a case by case basis. In an embodiment, the robotic motor drive and haptic feedback system is mounted proximal to the robotic arm end effector assembly. In another embodiment, the system is at a remote location. In the latter case the length and routing of the joint and end effector control cables can be completely variable and can be changed accordingly.

Figure 6:
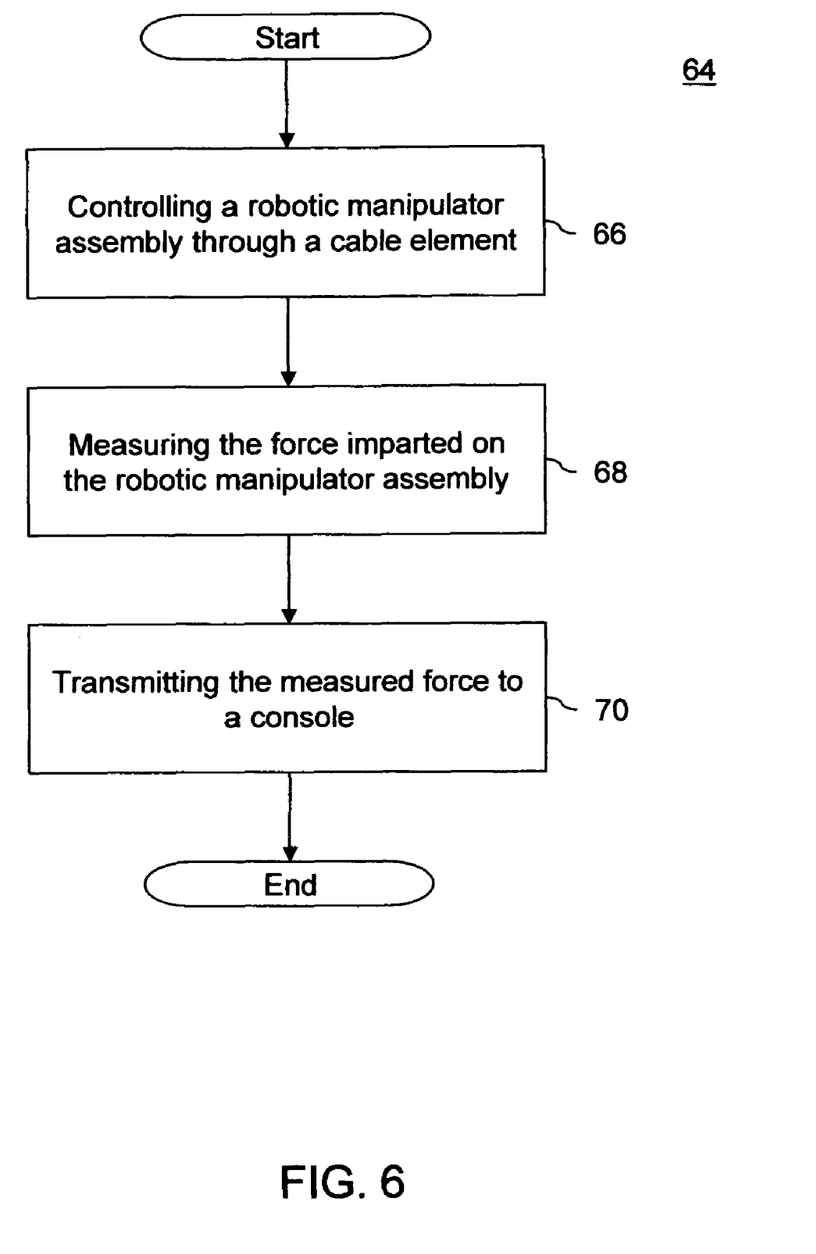
FIG. 6 illustrates a flowchart of a method for operating a robotic manipulator assembly, in accordance with an embodiment of the present application.

FIG. 6 illustrates a flowchart of a method for operating a robotic manipulator assembly, in accordance with an embodiment of the present application. The method 64 includes controlling a robotic manipulator assembly, such as one represented by system 10, through a cable element, such as cable element 48, for performing a medical procedure. The control procedure is as described for the figures above and is represented at step 66. The method further includes measuring the force imparted to the robotic manipulator assembly while it is performing the medical procedure. The force is measured by using a set of transducers, such as transducers 16 and 38, which along with an associated circuitry transform the measured force into a force feedback signal which is then transmitted to a user. The process of measuring the force and providing the force feedback signal to the user is as described for previous figures and is depicted at steps 68 and 70.

Various embodiments of the present application offer one or more advantages. The present application enables the operator in accurately estimating the forces that are required for performing medical procedures, as the noise generated due to environmental factors is removed. This also helps in precise automation of the process, thereby saving a lot of time and effort. Further, the system makes use of a single cable element for transmitting and measuring forces imparted during the medical procedure. This simplifies the system and eliminates noise that is created by the use of multiple cables. In addition, the system can also be employed where a single cable element is required to control multiple units, such as a crane for lifting and holding multiple items.

What is claimed is:

1. A system for performing a medical procedure, the system comprising:
   at least one robotic arm having one or more joints;
   at least one end effector for performing the medical procedure, the end effector being connected to the robotic arm assembly;
   a first set of actuators for driving the one or more joints;
   a second set of actuators for driving the end effector; and
   a cable element connecting the first set of actuators to the one or more joints and connecting the second set of actuators to the end effector, the cable element being configured to control the movement of the robotic arm and the end effector and to provide a force feedback signal to a user operating the system, the force feedback signal being generated on the basis of forces acting on the robotic arm and the end effector, and the force feedback signal configured to generate a vibration at a hand unit.

2. The system according to claim 1 further comprising one or more transducers for measuring the forces acting on the robotic arm and the end effector, the one or more transducers being connected to the cable element.

3. The system according to claim 1 further comprising a signal filter for filtering an unwanted signal from the force feedback signal.

4. The system according to claim 3 wherein the signal filter is a high pass filter.

5. The system according to claim 3 wherein the signal filter is a band-pass filter.

6. The system according to claim 1, wherein the movement of the robotic arm is controlled by driving the one or more joints.

7. The system according to claim 5, wherein the one or more joints are driven by the first set of actuators through the cable element.

8. The system according to claim 1, wherein the cable element connects the first set of actuators to the one or more joints of the robotic arm through one or more pulleys.

9. The system according to claim 1, wherein the cable element connects the second set of actuators to the end effector through one or more pulleys.

10. The system according to claim 1, wherein the first and second set of actuators are linear actuators.

11. The system according to claim 1, wherein the first and second set of actuators are motors.

12. The system according to claim 1 wherein the end effector is one of forceps, scissors, a needle driver, and an imaging device.

13. A system for performing a medical procedure, the system comprising:
   a robotic arm comprising one or more joints;
   at least one end effector for performing the medical procedure, the end effector being connected to the robotic arm assembly;
   a first set of actuators for driving to the one or more joints;
   a second set of actuators for driving the end effector;
   a cable element connecting the first set of actuators to the one or more joints and connecting the second set of actuators to the end effector, the cable element being configured to control the movement of the robotic arm and the end effector, the cable element also being configured to provide a force feedback signal to an operator operating the system, the force feedback signal being generated on the basis of forces acting on the robotic arm assembly and the end effector assembly, and the force feedback signal configured to generate a vibration at a hand unit;

one or more transducers for measuring the forces acting on the robotic arm and the end effector assembly, the one or more transducers being connected to the cable element; and a signal filter for filtering an unwanted signal from the force feedback signal.

14. A method for operating a robotic manipulator assembly comprising:

controlling the robotic manipulator assembly through a cable element, the robotic manipulator assembly being controlled for performing a medical procedure;

measuring the force imparted on the robotic manipulator assembly during the medical procedure, the force being measured by a set of transducers connected to the cable element; and providing a force feedback signal to a user operating the robotic manipulator assembly, the force feedback signal being based on the measured force, and the force feedback signal configured to generate a vibration at a hand unit.

15. The method according to claim 14, wherein the robotic manipulator assembly is controlled by:

a robotic arm assembly comprising
  a robotic arm comprising one or more joints;
  a first set of actuators for driving to the one or more joints;

an end effector assembly comprising:
  at least one end effector for performing the medical procedure, the end effector being connected to the robotic arm assembly;
  a second set of actuators for driving the end effector; and
  the cable element connecting the first set of actuators to the one or more joints and connecting the second set of actuators to the end effector.

16. The method according to claim 14 wherein controlling the robotic manipulator assembly further comprises:

controlling a robotic arm of the robotic manipulator assembly, the robotic arm being controlled through the cable element; and controlling an end effector of the robotic manipulator assembly, the end effector being controlled through the cable element.

17. The method according to claim 14 wherein the force is measured by one or more transducers connected to the cable element.

18. The method according to claim 14 further comprising filtering an unwanted signal from the force feedback signal.

19. The method according to claim 18 wherein the filtering is done using a high pass filter.

20. The method according to claim 18 wherein the filtering is done using a band-pass filter.

* * * * *